US011050686B2

(12) United States Patent
Koo

(10) Patent No.: US 11,050,686 B2
(45) Date of Patent: Jun. 29, 2021

(54) USER CARE SYSTEM USING CHATBOT

(71) Applicant: 1THEFULL PLATFORM LIMITED, Seoul (KR)

(72) Inventor: Seung-Yub Koo, Gyeonggi-do (KR)

(73) Assignee: 1THEFULL PLATFORM LIMITED, Seoul (KR)

( * ) Notice: Subject to any disclaimer, the term of this patent is extended or adjusted under 35 U.S.C. 154(b) by 0 days.

(21) Appl. No.: 16/648,352

(22) PCT Filed: May 30, 2018

(86) PCT No.: PCT/KR2018/006178
§ 371 (c)(1),
(2) Date: Mar. 18, 2020

(87) PCT Pub. No.: WO2019/059493
PCT Pub. Date: Mar. 28, 2019

(65) Prior Publication Data
US 2020/0228470 A1   Jul. 16, 2020

(30) Foreign Application Priority Data
Sep. 22, 2017 (KR) .......................... 10-2017-0122585

(51) Int. Cl.
*G06F 15/16* (2006.01)
*H04L 12/58* (2006.01)
(Continued)

(52) U.S. Cl.
CPC ............ *H04L 51/02* (2013.01); *A61B 5/0002* (2013.01); *A61B 5/165* (2013.01); *A61B 5/4803* (2013.01);
(Continued)

(58) Field of Classification Search
USPC ........................................................ 709/206
See application file for complete search history.

(56) References Cited

U.S. PATENT DOCUMENTS

2011/0283190 A1* 11/2011 Poltorak ............. H04L 12/2818
715/716
2017/0345324 A1* 11/2017 Fanty ...................... G10L 13/02
(Continued)

FOREIGN PATENT DOCUMENTS

JP   2007-004662 A   1/2007
KR   10-2004-0091000 A   10/2004
(Continued)

OTHER PUBLICATIONS

International Search Report for PCT/KR2018/006178 dated Sep. 7, 2018.

*Primary Examiner* — Alan S Chou
(74) *Attorney, Agent, or Firm* — The PL Law Group, PLLC

(57) ABSTRACT

A user care system accuses a chatbot. According to an embodiment of the present disclosure, not only a current state of a user can be quickly determined on the basis of a content of a conversation between a chatbot and the user, but also the user can quickly receive help from the outside when it is determined that the user is in a dangerous situation. Further, not only the chatbot can quickly determine a current state of the user on the basis of a change in biometric information of the user, but also the user can quickly receive help from the outside when it is determined that the user is in a dangerous situation.

9 Claims, 4 Drawing Sheets

(51) Int. Cl.
  *G16H 40/67* (2018.01)
  *G16H 50/30* (2018.01)
  *G06F 40/30* (2020.01)
  *A61B 5/00* (2006.01)
  *A61B 5/16* (2006.01)
  *G06N 5/04* (2006.01)
  *G06Q 50/26* (2012.01)
  *A61B 5/0205* (2006.01)
  *A61B 5/1455* (2006.01)
  *A61B 5/318* (2021.01)

(52) U.S. Cl.
  CPC ............ *G06F 40/30* (2020.01); *G06N 5/043* (2013.01); *G06Q 50/265* (2013.01); *G16H 40/67* (2018.01); *G16H 50/30* (2018.01); *A61B 5/02055* (2013.01); *A61B 5/14551* (2013.01); *A61B 5/318* (2021.01); *A61B 5/6801* (2013.01)

(56) References Cited

U.S. PATENT DOCUMENTS

| | | | | |
|---|---|---|---|---|
| 2018/0316631 | A1* | 11/2018 | Koukoumidis | G06N 3/006 |
| 2018/0330815 | A1* | 11/2018 | Demir | G16H 40/20 |
| 2018/0357286 | A1* | 12/2018 | Wang | G06K 9/6267 |
| 2020/0082928 | A1* | 3/2020 | Wu | G16H 80/00 |
| 2020/0118567 | A1* | 4/2020 | Horling | G06F 16/9535 |
| 2020/0137001 | A1* | 4/2020 | Wu | G06F 40/253 |

FOREIGN PATENT DOCUMENTS

| | | |
|---|---|---|
| KR | 10-2008-0024752 A | 3/2008 |
| KR | 10-0914633 B1 | 9/2009 |
| KR | 10-1322486 B1 | 10/2013 |
| KR | 10-2015-0063073 A | 6/2015 |
| KR | 10-2016-0074954 A | 6/2016 |
| KR | 10-2017-0064516 A | 6/2017 |

* cited by examiner

USER CARE SYSTEM USING CHATBOT

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2018/006178 filed on May 30, 2018, which claims priority to the benefit of Korean Patent Application No. 10-2017-0122585 filed in the Korean Intellectual Property Office on Sep. 22, 2017, the entire contents of which are incorporated herein by reference.

TECHNICAL FIELD

This disclosure relates to a user care system using a chatbot.

BACKGROUND ART

A conventional intelligent conversation robot is a chat robot that means a software agent capable of communicating with a person, and is called a chatterbot, a chatbot, a chatterbox, a conversation agent, or the like.

The intelligent conversation robot does not make a chat between a user and a user but makes a chat between a user and a chat agent, namely between a user and the intelligent conversation robot. Generally, the conversation robot stores expected question/answer pairs in a database by pattern matching in advance to answer a question of a user.

However, since most chat robots are able to answer only when the pattern is exactly matched with an input sentence (question), a large amount of dialogue examples are required, and thus a lot of cost is required to construct a dialogue example database (DB).

In addition, since the existing chat robots do not consider a dialogue context, a chat is performed to give a fixed answer to each question, regardless of past information.

Meanwhile, recently, a health care method has been developed to enable a user to know the analysis result of health information of a user in a short time using a wireless network and a mobile communication terminal.

However, in the conventional health care method, a user should directly input health information into the mobile communication terminal, which is inconvenient for the user to use the method. Further, at the present time in which the above intelligent conversation robot is gradually developed and advanced, there is a need to develop a technology that may interoperate the intelligent conversation robot with a user health (risk situation) management method.

SUMMARY

This disclosure is directed to providing a user care system using a chatbot, which may quickly determine a current state of a user through a conversation content of the chatbot and the user and also allow the user to receive help from the outside if it is determined that the user is in a dangerous situation.

In addition, the disclosure is directed to providing a user care system using a chatbot, in which the chatbot may quickly determine a current state of a user through the change of biometric information of the user and also allow the user to receive help from the outside if it is determined that the user is in a dangerous situation.

An embodiment of the present disclosure to accomplish the above technical object provides a user care system using a chatbot, which determines a current state of a user by using a chatbot mounted to a server, wherein the chatbot includes: a conversation content generating module configured to generate a conversation content information i1 and transmit the same to a user terminal of the user; a conversation content storing module configured to receive and store an answer content information i2 in response to the conversation content information i1 from the user terminal, an answer content base information i3 corresponding to the conversation content information i1 being stored in the conversation content storing module; and a determining module configured to determine a current state of the user by comparing the conversation content information i1, the answer content information i2 and the answer content base information i3.

In addition, the determining module may determine that the current state of the user is a dangerous situation, when the answer content information i2 is out of a preset matching ratio in comparison to the answer content base information i3.

In addition, the server may include a communication module configured to transmit a dangerous situation information i4 to an external terminal, when the current state of the user determined by the determining module is a dangerous situation.

In addition, the server may include a biometric information storing module configured to receive biometric information i5 of the user from a wearable device that the user is wearing and store the biometric information i5 at each preset unit time.

In addition, the determining module may compare a first biometric information i5-1 stored at a first unit time with a second biometric information i5-2 stored at a second unit time that is later than the first unit time, and determine that the current state of the user is a dangerous situation when the second biometric information i5-2 is out of a preset stable range in comparison to the first biometric information i5-1.

In addition, the server may include a communication module configured to transmit a dangerous situation information i6 to an external terminal, when the current state of the user determined by the determining module is a dangerous situation.

According to an embodiment of the present disclosure, it is possible to quickly determine a current state of a user through a conversation content of the chatbot and the user and also to allow the user to receive help from the outside if it is determined that the user is in a dangerous situation.

In addition, the chatbot may quickly determine a current state of a user through the change of biometric information of the user and also allow the user to receive help from the outside if it is determined that the user is in a dangerous situation.

DETAILED DESCRIPTION

Hereinafter, some embodiments of the present disclosure will be described in detail with reference to exemplary drawings. When adding reference symbols to components in each drawing, it should be noted that the same reference symbols are assigned to the same components as much as possible even though they are shown in different drawings. Also, in describing the present disclosure, if it is determined that a detailed description of the related known structure or function may obscure the gist of the present disclosure, the detailed description thereof will be omitted.

In addition, in describing a component of the present disclosure, terms such as "first", "second", "A", "B", "(a)" and "(b)" may be used. These terms are only for distinguishing the component from other components, and the nature, order or sequence of the components are not limited by the terms. If a component is described as being "connected", "coupled" or "contacted" to another component, that component may be directly connected or contacted to another component, but it is to be understood that another element may be further "connected", "coupled" or "contacted" between these components.

Figure 1:
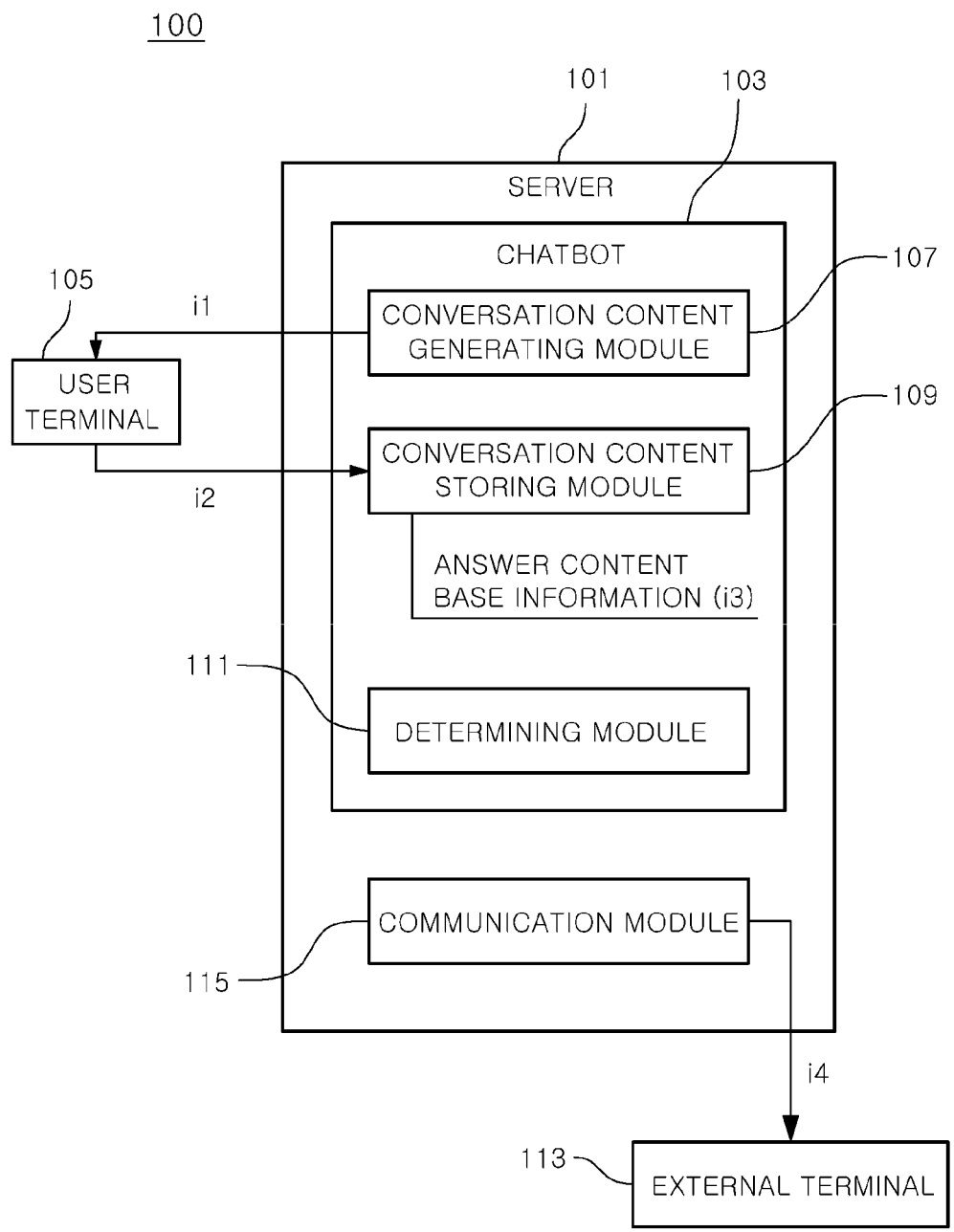
FIG. 1 is a block diagram showing a user care system using a chatbot according to an embodiment of the present disclosure.

FIG. 1 is a block diagram showing a user care system using a chatbot according to an embodiment of the present disclosure.

Figure 2:
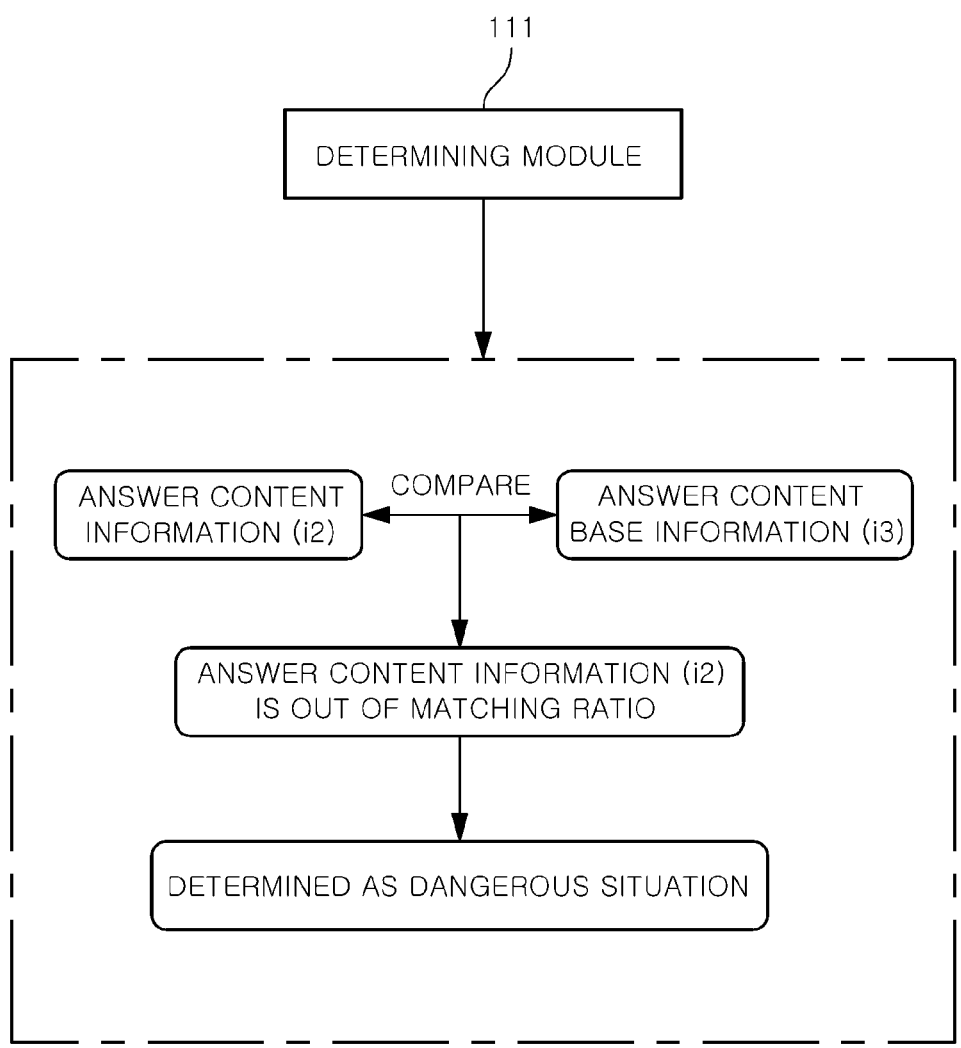
FIG. 2 is a diagram showing an example in which a determining module determines that a current state of a user is a dangerous situation, in the user care system using a chatbot of FIG. 1

FIG. 2 is a diagram showing an example in which a determining module determines that a current state of a user is a dangerous situation, in the user care system using a chatbot of FIG. 1

Figure 3:
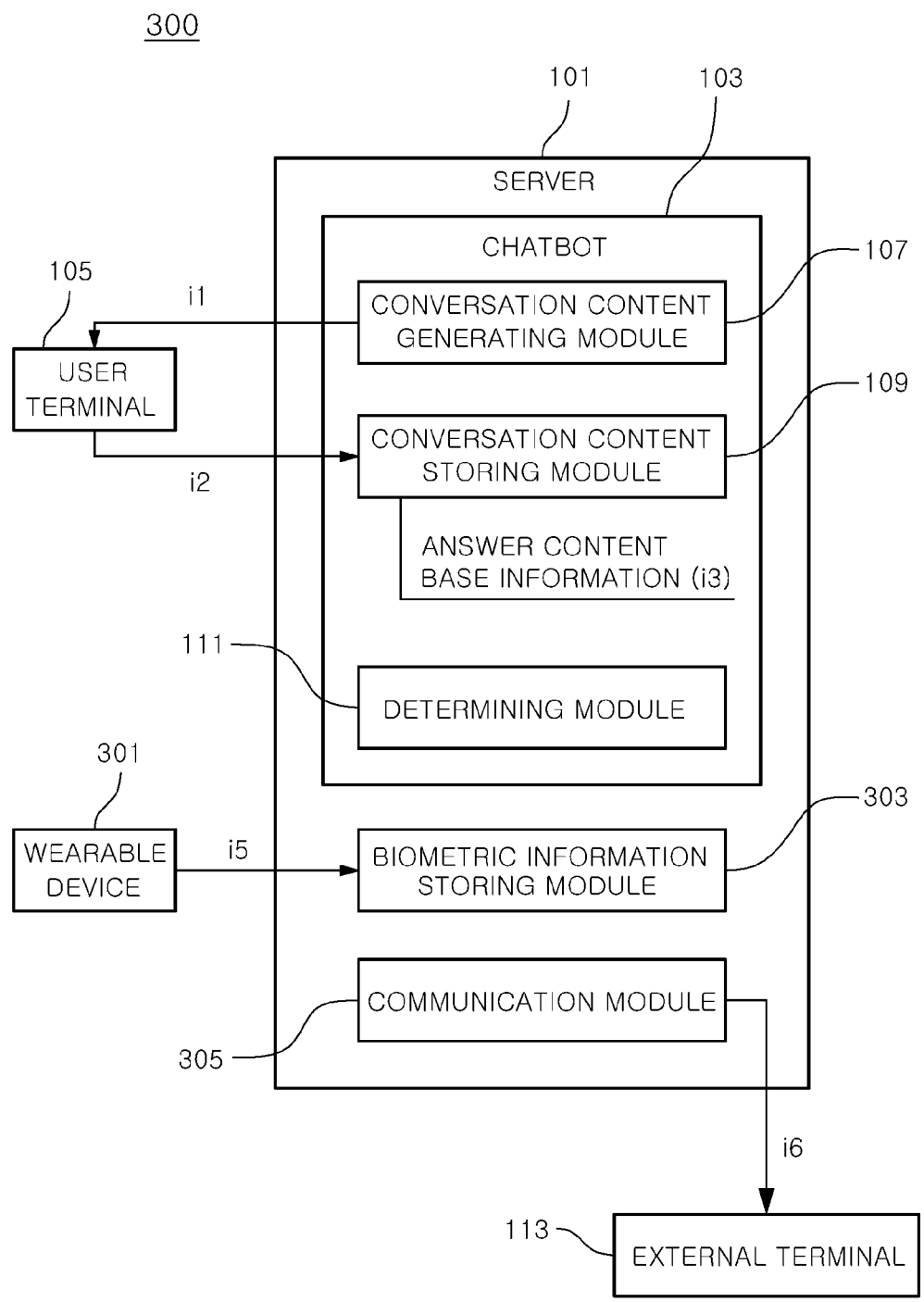
FIG. 3 is a block diagram showing a user care system using a chatbot according to another embodiment of the present disclosure.

FIG. 3 is a block diagram showing a user care system using a chatbot according to another embodiment of the present disclosure.

Figure 4:
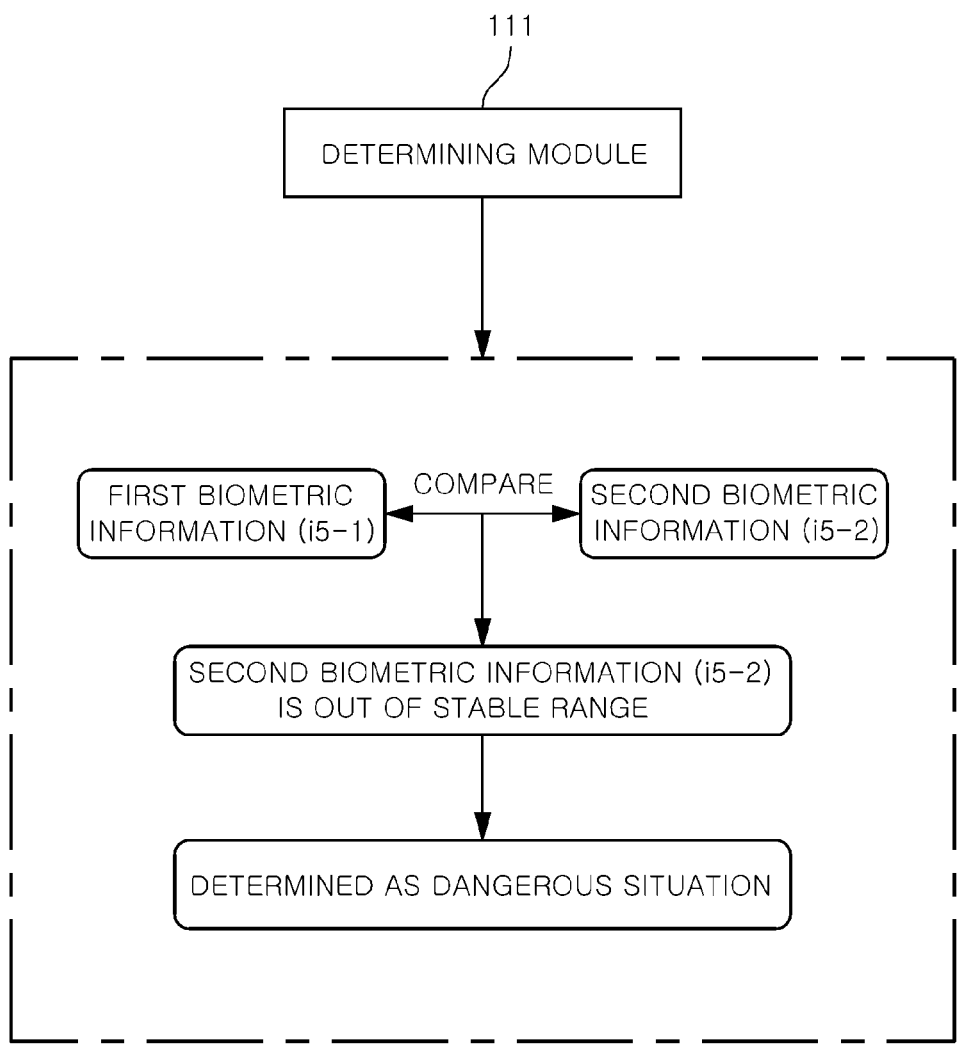
FIG. 4 is a diagram showing an example in which a determining module determines that a current state of a user is a dangerous situation, in the user care system using a chatbot of FIG. 3.

FIG. 4 is a diagram showing an example in which a determining module determines that a current state of a user is a dangerous situation, in the user care system using a chatbot of FIG. 3.

As shown in these figures, a user care system 100 using a chatbot according to an embodiment of the present disclosure is a care system that determines a current state of a user by using a chatbot 103 mounted to a server 101. Here, the chatbot 103 may include: a conversation content generating module 107 configured to generate a conversation content information i1 and transmit the same to a user terminal 105 of the user; a conversation content storing module 109 configured to receive and store an answer content information i2 in response to the conversation content information i1 from the user terminal 105, an answer content base information i3 corresponding to the conversation content information i1 being stored in the conversation content storing module 109; and a determining module 111 configured to determine a current state of the user by comparing the conversation content information i1, the answer content information i2 and the answer content base information i3.

Hereinafter, each structure is described in detail.

First, the present disclosure relates to a care system that determines a current state of a user by using the chatbot 103 mounted to the server 101.

Here, the chatbot 103 includes a conversation content generating module 107, a conversation content storing module 109, and a determining module 111.

The conversation content generating module 107 generates a conversation content information i1 and transmits the same to the user terminal 105 of the user.

The conversation content information i1 includes, for example, a question-type conversation content, a recommending-type conversation content, an informing-type conversation content, and the like.

Meanwhile, the conversation content information i1 includes a conversation content that is semantically and logically related to the answer content information i2 input from the user terminal 105.

For example, if the conversation content information i1 is a question-type conversation content of 'How are you feeling today?' and the answer content information i2 input from the user terminal 105 is 'I feel depressed today', the subsequent conversation content information i1 may be 'Watch a movie to change mood', or the like.

Subsequently, the conversation content storing module 107 receives and stores an answer content information i2 in response to the conversation content information i1 from the user terminal 105.

In addition, the conversation content storing module 109 stores an answer content base information i3 corresponding to the conversation content information i1.

That is, if the conversation content information i1 is 'How are you feeling today?' as in the above example, the conversation content storing module 109 stores the answer content information i2 of 'I feel depressed today' input from the user terminal 105.

In addition, the conversation content storing module 109 may include the answer content base information i3 (for example, logically and semantically related answer contents such as 'I feel good', 'I feel depressed', 'I feel refreshing' and 'condition not good') corresponding to the conversation content information i1.

Subsequently, the determining module 111 compares the conversation content information i1, the answer content information i2 and the answer content base information i3 to determine a current state of the user.

More specifically, the determining module 111 determines that the current state of the user is a dangerous situation, if the answer content information i2 is out of a preset matching ratio in comparison to the answer content base information i3.

For example, when the conversation content information i1 is 'How are you feeling today?', if the answer content information i2 'I feel depressed today' is matched with 'I feel depressed', 'condition not good' or the like stored in the answer content base information i3, the determining module 111 may determine that the current state of the user as a 'normal state'. However, if the answer content information i2 is 'I want to eat Chinese food', 'the weather is very hot today', or the like that is not matched with the information stored in the answer content base information i3, the determining module 111 may determine that the current state of the user is a 'dangerous situation'.

Since the chatbot 103 determines the current state of the user by using the conversation content information i1, the answer content information i2, the answer content base information i3, and the like, the current state of the user may be quickly and efficiently determined through the convent of conversation between the user and the chatbot 103.

Meanwhile, the server 101 includes a communication module 115 configured to transmit a dangerous situation information i4 to an external terminal 113 when the current state of the user determined by the determining module 111 is a 'dangerous situation'.

Here, the external terminal 113 may be, for example, a terminal operated by a hospital, a terminal operated by a 119 center (or, a rescue center), a terminal owned by a guardian, or the like.

Since the server 101 includes the communication module 115 for sending the dangerous situation information i4 to the external terminal 113, when the user is in a 'dangerous situation', the user may immediately receive help from the outside.

Meanwhile, in a user care system 300 using a chatbot according to another embodiment of the present disclosure, the server 101 includes a biometric information storing module 303 configured to receive biometric information i5 of the user from a wearable device 301 that the user wears and store the biometric information i5 at each preset unit time.

Here, the biometric information i5 may include electrocardiogram information, blood pressure information, oxygen saturation information, stress information, body temperature information, and the like of the user, and the 'preset unit time' may be, for example, '30 minutes' or '1 hour'.

In addition, the determining module 111 may compare first biometric information i5-1 stored at a first unit time (for example, stored at 1 p.m.) with second biometric information i5-2 stored at a second unit time (for example, stored at 2 p.m.) that is later than the first unit time, and determines that the current state of the user is a 'dangerous situation' if the second biometric information i5-2 is out of a preset stable range in comparison to the first biometric information i5-1.

For example, if the blood pressure information of the user stored at 2 p.m. (with a unit time of '1 hour') is 110 mmHg (relaxation phase)/160 mmHg (contraction phase) and the blood pressure information of the user stored at 1 p.m. (with a unit time of '1 hour') is 80 mmHg (relaxation phase)/120 mmHg (contraction phase), the determining module 111 determines that the blood pressure state of the user is outside the stable range (90 mmHg or below (relaxation phase)/140 mmHg or below (contraction phase)) at 2 p.m.

Since the determining module 111 may determine the current state of the user based on the biometric information of the user, it is possible to quickly detect whether the user is in a dangerous situation.

Meanwhile, the server 101 includes a communication module 305 configured to transmit dangerous situation information i6 to the external terminal 113 when the current state of the user determined by the determining module 111 is a dangerous situation.

Of course, this communication module 305 may include the functions of the communication module 115 described above.

Since the server 101 includes the communication module 305 for sending the dangerous situation information i6 to the external terminal 113, when the user is in a 'dangerous situation', the user may immediately receive help from the outside.

Meanwhile, if the user care system 300 using a chatbot according to another embodiment of the present disclosure as described above is used, even if the conversation content between the user and the chatbot 103 is normal, a dangerous situation of the user is determined by using the change in biometric information of the user, and the user may receive help from the outside.

As described above, according to an embodiment of the present disclosure, not only the current state of the user may be quickly determined through the conversation content between the chatbot and the user, but also the user may quickly receive help from the outside when it is determined that the user is in a dangerous situation.

Further, not only the chatbot may quickly determine a current state of the user on the basis of the change in biometric information of the user, but also the user may quickly receive help from the outside when it is determined that the user is in a dangerous situation.

Even though the preferred embodiment of the present disclosure has been illustrated and described above, the present disclosure is not limited to the specific preferred embodiment described above, and the present disclosure may be modified in various ways by those skilled in the art without departing from the scope of the present disclosure defined in the claims, and such modifications fall within the scope of the claims.

The invention claimed is:

1. A user care system using a chatbot, which determines a current state of a user by using a chatbot mounted to a server,
wherein the chatbot includes:
a processor;
a memory;
a conversation content generating module implemented by the processor, the conversation content generating module configured to generate a conversation content information and transmit the same to a user terminal of the user;
a conversation content storing module implemented by the processor and the memory, the conversation content storing module configured to receive and store an answer content information in response to the conversation content information from the user terminal, an answer content base information logically matched with the conversation content information being stored in the conversation content storing module;
a biometric information storing module implemented by the processor and the memory, the biometric information storing module configured to receive at least one of biometric information, electrocardiogram, blood pressure, oxygen saturation, and body temperature of the user from a wearable device that the user is wearing and store the biometric information at each preset unit time; and
a determining module implemented by the processor, the determining module configured to determine, by comparing the conversation content information, the answer content information and the answer content base information, that the current state of the user as a normal state if the answer content information is in a preset matching ratio in comparison to the answer content base information, and the biometric information is in a preset stable range, and, if not, the current state of the user as a dangerous situation.

2. The user care system using a chatbot according to claim 1, wherein the server is configured to transmit the dangerous situation information to an external terminal, when the current state of the user determined by the determining module is the dangerous situation.

3. The user care system using a chatbot according to claim 1, wherein the determining module compares a first biometric information stored at a first unit time with a second biometric information stored at a second unit time that is later than the first unit time, and determines that the current state of the user is the dangerous situation when the second biometric information is out of a preset stable range in comparison to the first biometric information.

4. A user care system, comprising:
a server; and
a chat robot mounted to the server, the chat robot comprising:
a memory configured to:
  receive and store an answer content information in response to a conversation content information from a user terminal, an answer content base information logically matched with the stored conversation content information;
  receive at least one of biometric information, electrocardiogram, blood pressure, oxygen saturation, and body temperature of the user from a wearable device that the user is wearing and store the biometric information at each preset unit time; and
a processor configured to:
  generate a conversation content information and transmit the same to the user terminal of the user; and
  determine, by comparing the conversation content information, the answer content information and the answer content base information, that the current state of the user as a normal state if the answer content information is in a preset matching ratio in comparison to the answer content base information, and the biometric information is in a preset stable range, and, if not, the current state of the user as a dangerous situation.

5. The user care system using a chatbot according to claim 4, wherein the server is configured to transmit the dangerous situation information to an external terminal, when the current state of the user is the dangerous situation.

6. The user care system using a chatbot according to claim 4, wherein the chatbot is configured to compare a first biometric information stored at a first unit time with a second biometric information stored at a second unit time that is later than the first unit time, and determines that the current state of the user is the dangerous situation when the second biometric information is out of a preset stable range in comparison to the first biometric information.

7. The user care system using a chatbot according to claim 4, wherein the chatbot is configured to compare a first biometric information stored at a first unit time with a second biometric information stored at a second unit time that is later than the first unit time, and determines that the current state of the user is the dangerous situation when the second biometric information is out of a preset stable range in comparison to the first biometric information.

8. A user care system, comprising:
a server; and
a chat robot mounted to the server, the chat robot configured to:
  generate a conversation content information and transmit the same to a user terminal of the user;
  receive and store an answer content information in response to the conversation content information from the user terminal, an answer content base information logically matched with the conversation content information;
  receive at least one of biometric information, electrocardiogram, blood pressure, oxygen saturation, and body temperature of the user from a wearable device that the user is wearing and store the biometric information at each preset unit time; and
  determine, by comparing the conversation content information, the answer content information and the answer content base information, that the current state of the user as a normal state if the answer content information is in a preset matching ratio in comparison to the answer content base information, and the biometric information is in a preset stable range, and, if not, the current state of the user as a dangerous situation; and
an external terminal receiving the determined current state of the user.

9. The user care system using a chatbot according to claim 8, wherein the server is configured to transmit the dangerous situation information to the external terminal, when the current state of the user is the dangerous situation.

* * * * *

UNITED STATES PATENT AND TRADEMARK OFFICE
CERTIFICATE OF CORRECTION

PATENT NO.        : 11,050,686 B2
APPLICATION NO.   : 16/648352
DATED             : June 29, 2021
INVENTOR(S)       : Seung-Yub Koo Page 1 of 1

It is certified that error appears in the above-identified patent and that said Letters Patent is hereby corrected as shown below:

In the Specification

Column 1, Line 2, add:
-- GOVERNMENT RIGHTS IN INVENTION
This invention was made with Korean government support under Project No. S2783429 (Research Program: New product development project with conditions for purchase) awarded by Korea Technology & Information Promotion Agency for SMEs for the Research subject of "Development of a smart store service platform based on AI hologram terminals", carried out by Wonderfulplatform. The Korean government has certain rights in the invention. --

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*